United States Patent
Rautou et al.

(10) Patent No.: US 11,231,422 B2
(45) Date of Patent: Jan. 25, 2022

(54) METHODS AND KITS FOR PREDICTING THE RISK OF HAVING OR DEVELOPPING HEPATOCELLULAR CARCINOMA IN PATIENTS SUFFERING FROM CIRRHOSIS

(71) Applicants: INSERM (Institute National de la Santé et de la Recherche Médicale), Paris (FR); Université Paris Descartes, Paris (FR); Assistance Publique-Hôpitaux de Paris (APHP), Paris (FR); Université Paris Diderot—Paris 7, Paris (FR)

(72) Inventors: Pierre-Emmanuel Rautou, Paris (FR); Chantal Boulanger-Robert, Paris (FR)

(73) Assignees: INSERM (Institut National de la Santé et de la Recherche Médicale), Paris (FR); Université Paris Descartes, Paris (FR); Assistance Publique Hôpitaux de Paris (APHP), Paris (FR); UniversitéParis Diderot—Paris 7, Paris (FR)

( * ) Notice: Subject to any disclaimer, the term of this patent is extended or adjusted under 35 U.S.C. 154(b) by 11 days.

(21) Appl. No.: 16/495,287

(22) PCT Filed: Mar. 20, 2018

(86) PCT No.: PCT/EP2018/057020
§ 371 (c)(1),
(2) Date: Sep. 19, 2019

(87) PCT Pub. No.: WO2018/172357
PCT Pub. Date: Sep. 27, 2018

(65) Prior Publication Data
US 2020/0033349 A1 Jan. 30, 2020

(30) Foreign Application Priority Data
Mar. 21, 2017 (EP) ..................... 17305316

(51) Int. Cl.
G01N 33/574 (2006.01)
C07K 16/28 (2006.01)
G01N 33/569 (2006.01)

(52) U.S. Cl.
CPC ... G01N 33/57438 (2013.01); C07K 16/2854 (2013.01); G01N 33/56966 (2013.01)

(58) Field of Classification Search
CPC ....... G01N 33/57438; G01N 33/56966; C07K 16/2854
See application file for complete search history.

(56) References Cited

PUBLICATIONS

Campello et al. Circulating microparticles in cirrhotic patients with hepatocellular carcinoma (HCC) and portal vein thrombosis. Thrombosis Research 133S2. S195. PO-16 (2014).*

(Continued)

*Primary Examiner* — Gailene Gabel
(74) *Attorney, Agent, or Firm* — W & C IP

(57) ABSTRACT

Plasma levels of different sub-populations of microvesicles (endothelial, leukocyte, platelet and hepatocyte) were measured by flow cytometry or ELISA/filtration on blood samples from 125 patients with cirrhosis, for which 36 of them were diagnosed with HCC at inclusion. The inventors show that the levels of microvesicles of endothelial origin (CD62E+) could predict the occurrence of HCC in patients with cirrhosis. Therefore the present invention relates to a method for determining whether a patient suffering from cirrhosis is at risk of having or developing hepatocellular carcinoma comprising determining the level of endothelial-derived microvesicles (e.g. by flow cytometry) in a blood sample obtained from the patient.

9 Claims, 1 Drawing Sheet

(56) References Cited

PUBLICATIONS

Brodsky et al. Dynamics of Circulating Microparticles Liver Transplant Patients. J Gastrointestin Liver Dis. 17 (3): 261-268 (Sep. 2008).*

Campello et al. Circulating microparticles in cirrhotic patients with hepatocellular carcinoma (HCC) and portal vein thrombosis. Thrombosis Research 134S2. S88. OC-177 (Nov. 18, 2014).*

Bennett et al. Sonographic Detection of Hepatocellular Carcinoma and Dysplastic Nodules in Cirrhosis: Correlation of Pretransplantation Sonography and Liver Explant Pathology in 200 Patients. AJR 179: 75-80 (2002).*

Ferrin et al.; "Plasma Protein Biomarkers of Hepatocellular Carcinoma in HCV-Infected Alcoholic Patient with Cirrhosis"; PLOS One, vol. 10, No. 3, Mar. 19, 2015, p. e0118527.

Campello et al.; "Hypercoagulability detected by circulating microparticles in patients hepatocellular carcinoma and cirrhosis"; Thrombosis Research, vol. 143, May 20, 2016, pp. 118-121.

Vital et al.; "7th ITHIC Abstracts: Posters"; Thrombosis Research, vol. 133, 2014, abstract PO-16 on p. S195.

Barco; "Oral communciations"; Thrombosis Research, vol. 134, 2014, abstract OC117 on p. S88.

Zanetto et al.; "Circulating microparticles and risk of portal vein thrombosis in patients with liver cirrohsis and hepatocellular carcinoma"; Digestive and Liver Disease, vol. 48,2016, abstract T-41.

Zanetto et al. "OC.03.7 Circulating microparticles and risk of portal vein thrombosis in patients with liver cirrohsis and hepatocellular carcinoma"; Digestive and Liver Disease, vol. 48, 2016, abstract OC.03.7.

* cited by examiner

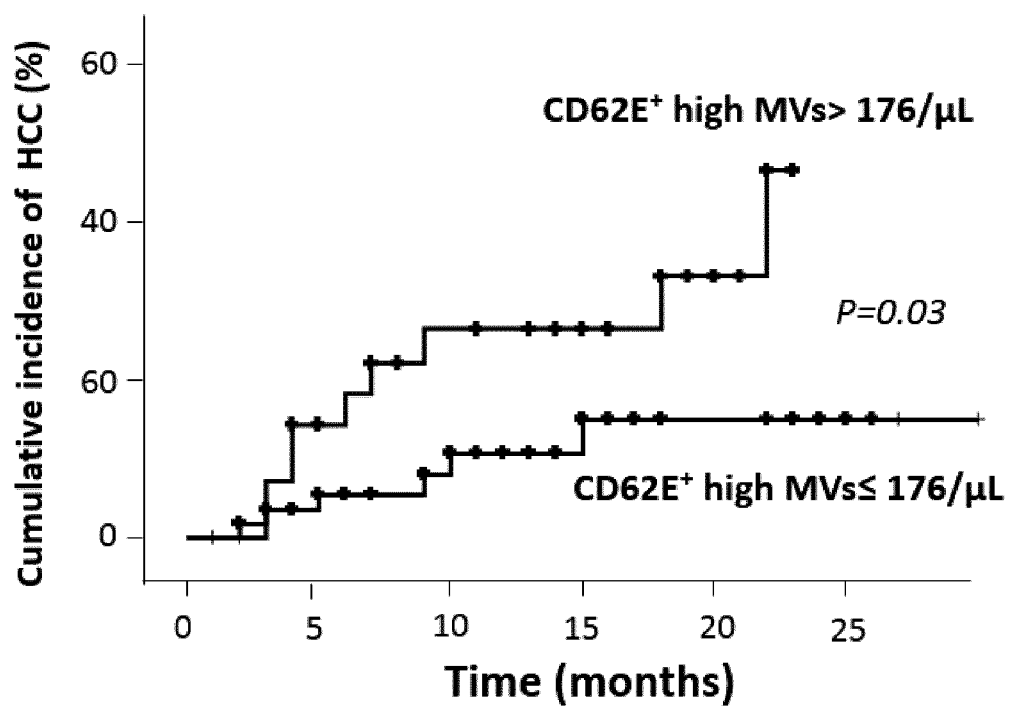

METHODS AND KITS FOR PREDICTING THE RISK OF HAVING OR DEVELOPPING HEPATOCELLULAR CARCINOMA IN PATIENTS SUFFERING FROM CIRRHOSIS

FIELD OF THE INVENTION

The present invention relates to methods and kits for predicting the risk of having or developing hepatocellular carcinoma in patients suffering from cirrhosis.

BACKGROUND OF THE INVENTION

Currently, hepatocellular carcinoma (HCC) is the third leading cause of cancer-related death worldwide and one of the leading causes of death among patients with cirrhosis. The incidence of HCC in the United States is increasing due to the current epidemic of hepatitis C virus (HCV) infection and non-alcoholic fatty liver disease (NAFLD). Prognosis for patients with HCC depends on tumor stage, with curative options available for patients diagnosed at an early stage. Patients with early HCC achieve five-year survival rates of seventy percent with resection or transplantation, whereas those with advanced HCC have a median survival of less than one year. Frequently, surveillance methods use ultrasound with or without alpha fetoprotein (AFP) every six months to detect HCC at an early stage. Such methods are recommended in high-risk populations. However, one difficulty in developing an effective surveillance program is the accurate identification of a high-risk target population. Patients with cirrhosis are at particularly high risk for developing HCC, but this may not be uniform across all patients and etiologies of liver disease. Retrospective case-control studies have identified risk factors for HCC among patients with cirrhosis, such as older age, male gender, diabetes, and alcohol intake, and subsequent studies have developed predictive regression models for the development of HCC using several of these risk factors. However, these predictive models are limited by moderate accuracy.

SUMMARY OF THE INVENTION

The present invention relates to methods and kits for predicting the risk of having or developing hepatocellular carcinoma in patients suffering from cirrhosis. In particular, the present invention is defined by the claims.

BRIEF DESCRIPTION OF THE DRAWINGS

The accompanying drawing, which is incorporated in and constitutes a part of this specification, illustrates embodiments of the invention and, together with a general description of the invention given above and the detailed description given below, serves to explain the invention.

FIG. 1 shows the cumulative risk of developing hepatocellular carcinoma in patients with cirrhosis according to circulating levels of endothelial microvesicles (CD62E+).

DETAILED DESCRIPTION OF THE INVENTION

The first object of the present invention relates to a method for determining whether a patient suffering from cirrhosis is at risk of developing or having hepatocellular carcinoma comprising i) determining the level of endothelial-derived microvesicles in a blood sample obtained from the patient and ii) comparing the level determined at step i) with a predetermined reference value wherein a difference between the level determined at step i) and the predetermined reference value is indicative of risk of the patient of developing or having hepatocellular carcinoma.

As used herein, the term "cirrhosis" refers to a consequence of chronic liver disease characterized by replacement of liver tissue by fibrosis, scar tissue and regenerative nodules (lumps that occur as a result of a process in which damaged tissue is regenerated), leading to loss of liver function. Cirrhosis is most commonly caused by alcoholism, hepatitis B and C, and fatty liver disease (e.g. non-alcoholic steatohepatitis), but has many other possible causes.

As used herein, the term "hepatocellular carcinoma" or "HCC" refers to a malignant tumor of hepatocellular origin that may develop in patients with cirrhosis. HCC is a type of liver cancer. HCC can undergo hemorrhage and necrosis because of a lack of fibrous stroma. Vascular invasion, particularly of the portal system, is common. Aggressive HCC can cause hepatic rupture and hemoperitoneum.

As used herein, the term "risk" relates to the probability that an event will occur over a specific time period, as in the conversion to HCC, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. Alternative continuous measures which may be assessed in the context of the present invention include time to HCC conversion and therapeutic HCC conversion risk reduction ratios. "Risk evaluation," or "evaluation of risk" in the context of the present invention encompasses making a prediction of the probability, odds, or likelihood that an event or disease state may occur, the rate of occurrence of the event or conversion from one disease state to another, i.e., from a normal condition to HCC or to one at risk of developing HCC. Risk evaluation can also comprise prediction of future clinical parameters, traditional laboratory risk factor values, or other indices of HCC, such as alcohol consumption or cigarette smoking, either in absolute or relative terms in reference to a previously measured population. The methods of the present invention may be used to make continuous or categorical measurements of the risk of conversion to HCC, thus diagnosing and defining the risk spectrum of a category of subjects defined as being at risk for HCC. In the categorical scenario, the invention can be used to discriminate between normal and other subject cohorts at higher risk for HCC.

As used herein the term "blood sample" means a whole blood, serum, or plasma sample obtained from the patient. Preferably the blood sample, according to the invention, is a plasma sample. A plasma sample may be obtained using methods well known in the art. For example, blood may be drawn from the patient following standard venipuncture procedure on tri-sodium citrate buffer. Plasma may then be obtained from the blood sample following standard procedures including but not limited to, centrifuging the blood sample at about 2500*g for about 15 minutes (room temperature), followed by pipeting of the plasma layer. Platelet-free plasma (PFP) will be obtained following a second centrifugation at about 2500*g for 15 min. Analyses can be performed directly on this PFP. Alternatively, microvesicles (MVs) may be more specifically isolated by further centrifuging the PFP at about 15,000 to about 25,000*g at 4° C. Different buffers may be considered appropriate for resuspending the pelleted cellular debris which contains the MVs. Such buffers include reagent grade (distilled or deionized) water and phosphate buffered saline (PBS) pH 7.4 or NaCl 0.9%. Preferably, PBS buffer (Sheath fluid) is used.

As used herein the term "microvesicle" or "MV" has its general meaning in the art and denotes a plasma membrane vesicle shed from an apoptotic or activated cell. The size of microvesicles ranges from 0.1 µm to 1 µm in diameter. The surface markers of microvesicles are the same as the cells from they originated. As used herein, the term "endothelial-derived microvesicle" refers to a microvesicle that derives from an endothelial cell. In particular endothelial-derived microvesicles are characterized by the expression of CD62E. Thus in some embodiments, the method of the present invention comprises determining the level of endothelial CD62E+ microvesicles. As used herein, the term "CD62E" has its general meaning in the art and refers to E-selectin, also known as CD62 antigen-like family member E (CD62E), endothelial-leukocyte adhesion molecule 1 (ELAM-1), or leukocyte-endothelial cell adhesion molecule 2 (LECAM2). An exemplary human amino acid sequence is represented by the NCBI reference sequence NP_000441.

Standard methods for determining the level of microvesicles in a blood sample are well known in the art. For example the methods may consist in collecting a population of microvesicles from a patient and using differential binding partners directed against the specific surface markers of said microvesicles, wherein microvesicles are bound by said binding partners to said surface markers.

In some embodiments, the binding partner may be an antibody that may be polyclonal or monoclonal, preferably monoclonal, directed against the specific surface marker of microvesicles. Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies of the invention or a fragment thereof can be prepared and isolated using any technique that provides for the production of antibody molecules by continuous cell lines in culture. Techniques for production and isolation include but are not limited to the hybridoma technique; the human B-cell hybridoma technique; and the EBV-hybridoma technique.

In some embodiments, the blood sample is contacted with an antibody specific for CD62E (positive selection).

In some embodiments, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library.

In some embodiments, the binding partner of the invention is labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody or aptamer, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as $I^{123}$, $I^{124}$, $In^{111}$, $Re^{186}$, $Re^{188}$. Preferably, the antibodies against the surface markers are already conjugated to a fluorophore (e.g. FITC-conjugated and/or PE-conjugated).

The aforementioned assays may involve the binding of the binding partners (i.e. antibodies or aptamers) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. The solid surfaces are preferably beads. Since microvesicles have a diameter of roughly 0.1 to 1 µm, the beads for use in the present invention should have a diameter larger than 1 µm. Beads may be made of different materials, including but not limited to glass, plastic, polystyrene, and acrylic. In addition, the beads are preferably fluorescently labelled.

According to the invention, methods of flow cytometry are preferred methods for determining the level of microvesicles in the blood sample obtained from the patient. For example, fluorescence activated cell sorting (FACS) may be therefore used to separate in the blood sample the desired microvesicles. In another embodiment, magnetic beads may be used to isolate microvesicles (MACS). For instance, beads labelled with monoclonal specific antibodies may be used for the positive selection of microvesicles. Other methods can include the isolation of microvesicles by depletion of non microvesicles components (negative selection). For example, microvesicles may be excited with 488 nm light and logarithmic green and red fluorescences of FITC and PE may be measured through 530/30 nm and 585/42 nm bandpass filters, respectively. The absolute number of microvesicles may then be calculated through specific software useful in practicing the methods of the present invention. Accordingly, in a specific embodiment, the method of the invention comprises the steps of obtaining a blood sample as above described; putting said prepared sample into a container; adding both labeled antibodies against surface markers that are specific to microvesicles of interest, and a known concentration of fluorescent solid surfaces; performing a FACS analysis on the prepared sample in order to calculate the absolute number of microvesicles therein.

In some embodiments, an ELISA method is used, wherein the wells of a microtiter plate are coated with a set of antibodies which recognize said the microvesicle of interest. The blood sample is then added to the coated wells. After a period of incubation sufficient to allow the formation of antibody-antigen complexes, the plate(s) can be washed to remove unbound moieties and a detectably labelled secondary binding molecule is added. The secondary binding molecule is allowed to react with any captured sample marker protein, the plate washed and the presence of the secondary binding molecule detected using methods well known in the art. Specificity for microvesicles can be obtained by filtrating the plasma.

Typically, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of expression levels in properly banked historical patient samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after quantifying the expression level in a group of reference, one can use algorithmic analysis for the statistic treatment of the determined levels in samples to be tested, and thus obtain a classification standard having significance for sample classification. The full name of ROC curve is Receiver Operator Characteristic Curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined reference value was established in a population of patients who did not have nor did not develop hepatocellular carcinoma when blood was drawn. Accordingly when the level of microvesicles is higher than the predetermined reference value, it is concluded that the patient is at risk of developing hepatocellular carcinoma. On contrary, when the level of microvesicles is lower than the predetermined reference value, then is it concluded that the patient is not at risk of developing hepatocellular carcinoma. In some embodiments, high statistical significance values (e.g. low P values) are obtained for a range of successive arbitrary quantification values, and not only for a single arbitrary quantification value. Thus, in some embodiments, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, according to this specific embodiment of a "cut-off" value, the outcome can be determined by comparing the expression level with the range of values which are identified. In some embodiments, a cut-off value thus consists of a range of quantification values, e.g. centered on the quantification value for which the highest statistical significance value is found (e.g. generally the minimum p value which is found). For example, on a hypothetical scale of 1 to 10, if the ideal cut-off value (the value with the highest statistical significance) is 5, a suitable (exemplary) range may be from 4-6. For example, a patient may be assessed by comparing values obtained by determining the level of microvesicles, where values greater than 5 reveal that the patient is at risk of developing HCC and values less than 5 reveal that the patient is not at risk of developing HCC. In some embodiments, a patient may be assessed by comparing values obtained by measuring the level of microvesicles and comparing the values on a scale, where values above 6 indicate that the patient is at risk of developing HCC and values below 4 indicate that the patient is not at risk of developing HCC, with values falling within the range of 4-6 indicating an intermediate risk.

The result given by the method of the invention may be used as a guide in determining how frequently HCC should be screened using imaging procedures, in selecting a therapy or treatment regimen for the patient. For example, when the patient has been determined as having a high risk of HCC development, he can be eligible for ultrasonography every 3 months instead of 6 months.

A further object of the invention relates to a kit for performing the method of the invention comprising means for determining the level of endothelial-derived microvesicles in a blood sample obtained from said patient. The kit may include a set of antibodies as above described. In some embodiments, the antibody or set of antibodies are labelled as above described. The kit may also contain other suitably packaged reagents and materials needed for the particular detection protocol, including solid-phase matrices, if applicable, and standards. Typically, the kits described above will also comprise one or more other containers, containing for example, wash reagents, and/or other reagents capable of quantitatively detecting the presence of bound antibodies. Typically compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the blood sample, a container which contains the antibody(s) used in the assay, containers which contain wash reagents (such as phosphate buffered saline, Tris-buffers, and like), and containers which contain the detection reagent.

The invention will be further illustrated by the following FIGURES and examples. However, these examples and FIGURES should not be interpreted in any way as limiting the scope of the present invention.

FIGURE

FIG. 1: Cumulative risk of developing hepatocellular carcinoma in patients with cirrhosis according to circulating levels of endothelial microvesicles (CD62E+).

EXAMPLE

Plasma levels of different sub-populations of microvesicles (endothelial, leukocyte, platelet and hepatocyte) were measured by flow cytometry or ELISA/filtration on blood samples from 125 patients with cirrhosis, including 36 with a diagnosed with HCC at inclusion. Among the 89 patients without HCC diagnosed at inclusion and monitored prospectively by scan and/or ultrasound for 12 months, 15 developed HCC during follow-up. The capacity of circulating levels of microvesicles to predict the occurrence of HCC has been tested by the actuarial Kaplan Meier method. Results are expressed as median (interquartile range) or number of patients (%).

The 36 patients with active HCC at inclusion had less severe cirrhosis than the 89 patients without HCC [MELD at 11 (7-25) vs. 13 (10-16); P=0.027]. In order to determine whether the existence of HCC affected the levels of plasma microvesicles independently of severity and cause of cirrhosis, we performed a case-control study. We have matched the cause of cirrhosis and the severity of cirrhosis 21 of the 36 patients with HCC at inclusion with 21 of the 89 patients not having HCC at inclusion. The only difference between the 2 groups was that the rate of platelet-derived microvesicles (CD41+) slightly higher in the 21 patients with cirrhosis with HCC [729 (416-1688) vs. 606 (279-1566); P=0.026]. We then analyzed the impact of the size of the HCC nodule on the levels of microvesicles in the 36 patients with HCC. We did not see any difference between patients with a tumor volume greater than 5 cm3 and those with a volume below this limit. We then analyzed the ability of microvesicle levels to predict the occurrence of HCC in 89 patients without HCC at inclusion. Patients who developed HCC in the follow-up had 2-fold higher rates of endothelial microvesicles (CD62E+, p=0.032) microvesicle than patient who did not develop the cancer. The actuarial risk to develop HCC was 26% at 12 months in patients having level of microvesicles of endothelial origin in the 3rd tertile vs. 11% in others (log rank, p=0.03).

Our results show that the levels of microvesicles are not very different in patients with and without HCC when the tumor is small, a situation where there is a clinical need. In contrast, microvesicles of endothelial origin (CD62E+) could predict the occurrence of HCC in patients with cirrhosis.

REFERENCES

Throughout this application, various references describe the state of the art to which this invention pertains. The disclosures of these references are hereby incorporated by reference into the present disclosure.

The invention claimed is:

1. A method for determining whether a patient suffering from cirrhosis is at risk of developing hepatocellular carcinoma and monitoring the patient identified as at risk, comprising
contacting plasma obtained from a blood sample from the patient with at least one differential binding partner, wherein the at least one differential binding partner is directed against a specific surface marker on an endothelial-derived microvesicle and wherein binding of the at least one differential binding partner to a specific cell surface marker enables differentiation of the endothelial-derived microvesicle from a microvesicle derived from another cell selected from the group consisting of leukocyte, platelet and hepatocyte;
measuring a level of the endothelial-derived microvesicles which bound to the at least one differential binding partner in the plasma, wherein
the level of endothelial-derived microvesicles is determined to be higher than a predetermined reference value,
monitoring the patient when the level of the measured endothelial-derived microvesicles is higher than the predetermined reference value and thus is indicative of being at risk of developing hepatocellular carcinoma, wherein said monitoring is performed using an imaging procedure configured to detect hepatocellular carcinoma, and
providing to the patient suffering from cirrhosis a treatment for hepatocellular carcinoma when detected by the imaging procedure, wherein said treatment is selected from the group consisting of resection of the patient's liver and transplantation of a liver into the patient.

2. The method of claim 1, wherein the at least one binding partner is a monoclonal antibody.

3. The method of claim 2, wherein the monoclonal antibody is specific for binding to a cell-surface marker E-selectin CD62E.

4. The method of claim 1, wherein the measuring step is performed using flow cytometry.

5. The method of claim 1, wherein the predetermined reference value is derived from a population of patients who do not have hepatocellular carcinoma.

6. The method of claim 5, wherein the population of patients used for deriving the predetermined reference value are known to have cirrhosis.

7. The method of claim 1, wherein said imaging procedure configured to detect hepatocellular carcinoma comprises conducting a scan and/or ultrasonography of the patient at every three months for at least 12 months.

8. The method of claim 1, wherein said treating comprises resection of the patient's liver.

9. The method of claim 1, wherein said treating comprises transplantation of a liver into the patient.

* * * * *